United States Patent
Beard

(10) Patent No.: US 6,960,677 B1
(45) Date of Patent: Nov. 1, 2005

(54) PREPARATION OF ALUMINATES

(75) Inventor: William R. Beard, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 121 days.

(21) Appl. No.: 10/696,750

(22) Filed: Oct. 28, 2003

(51) Int. Cl.$^7$ .............................. C07F 5/06; C25D 3/00
(52) U.S. Cl. ..................................... 556/187; 205/237
(58) Field of Search ........................ 556/187; 205/237

(56) References Cited

U.S. PATENT DOCUMENTS

| | | | |
|---|---|---|---|
| 2,849,349 A | 8/1958 | Ziegler et al. | |
| 3,234,115 A | 2/1966 | Ziegler et al. | |
| 3,254,009 A | 5/1966 | Ziegler et al. | |
| 3,255,224 A * | 6/1966 | Ziegler et al. | 556/187 |
| 3,285,947 A | 11/1966 | Ziegler et al. | |
| 3,324,159 A * | 6/1967 | Grimme et al. | 556/181 |
| 3,361,781 A | 1/1968 | Ziegler et al. | |
| 3,766,234 A | 10/1973 | Kirsch | |
| 3,969,195 A | 7/1976 | Dotzer et al. | |
| 6,734,317 B2 * | 5/2004 | Heitmann et al. | 556/187 |

OTHER PUBLICATIONS

Ahmad, N., et al., "Ligand Exchange in Tetraalkylaluminate Ions: Catalysis by the Sodium Ion", Organometallics, vol 3, 1984, pp. 389-392.

Grosse, A.V., et al., "Organoaluminum Compounds I. Methods of Preparation", J. Org. Chem., vol. 5, 1940, pp. 106-121.

Hoberg, H., et al., "Radikalische Zwischenstufen Bei Der Bildung von Kaliumtetraethylaluminat Aus Triethylaluminium Und Kalium", J. of Organometallic Chemistry, vol 184, 1980, pp. 1-5. Abstract only translated.

Lehmkuhl, H., "Complex Formation with Organoaluminum Compounds", Agnew. Chem. Internat. Edit., vol. 3, No. 2, 1965, pp. 107-114.

Lehmkuhl, H., et al., "Deposition of Aluminum—Magnesium Alloys from Electrolytes Containing Organo-Aluminum Complexes", Advanced Engineering Materials, vol. 3, No. 6, 2001, pp. 412-417.

Lehmkuhl, H., et al., "Elektrolytische Abscheidung von Aluminium-Magnesium-Ligierungen aus aliminiumorganischen Komplexelektrolyten", Mat.-wiss. U. Werkstofftech. vol. 31, 2000, pp. 889-898. Abstract only translated.

Lehmkuhl, H., et al., "Organometallic compounds. XLIV. Electrochemical Studies on the Synthesis of Ethyl Metal Compounds", Justus Liebigs Ann. Chem., 1967, 705, pp. 1-22. Chemical Abstracts, vol. 67, 1967, column 73639, item 73639h, 1 page.

Mole, T., et al., Organoaluminum Compounds, Chapter 7, Organoaluminates, New York, Elsevier Publishing Co., 1972, pp. 167-204.

Schaschel, E., et al., "Ion-Solvent Interactions. Solvationof the Sodium Ion", J. of the Am. Chem. Soc., vol. 90:2, Jan. 17, 1968, pp. 503-504.

Zakharkin L.I., et al., "Complexes of Trialkylaluminums and Dialkylaluminum Hydrides with Alkyls of Alkali Metals and Metals and Their Hydrides", J. of General Chemistry of the USSR, vol. 32, 1962, pp. 688-690.

Excerpts from "Salt-like Complexes with Tetravalent Aluminum via Multistep Reactions", Heuben-Weyl, vol. XIII, No. 4, 1970, pp. 127-132.

* cited by examiner

*Primary Examiner*—Porfirio Nazario-Gonzalez
(74) *Attorney, Agent, or Firm*—Marcy M. Hoefling

(57) ABSTRACT

A process for producing a tetrahydrocarbylaluminate is provided. This process comprises contacting sodium potassium alloy and a trihydrocarbylaluminum compound such that a tetrahydrocarbylaluminate is formed as a mixture of its sodium salt and potassium salt.

28 Claims, No Drawings

PREPARATION OF ALUMINATES

TECHNICAL FIELD

This invention relates to the preparation of tetrahydrocarbylaluminates from trihydrocarbylaluminum compounds. Tetrahydrocarbylaluminates are useful as electrolytes, especially for electrodeposition of aluminum.

BACKGROUND

There are several reports of the reaction of individual alkali metals with trialkylaluminum compounds to form the corresponding tetraalkylaluminates as their alkali metal salts, particularly from either sodium metal or potassium metal. The reaction between an alkali metal and a trialkylaluminum compound is often represented as:

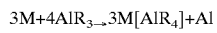

where M is the alkali metal and R is an alkyl group. See for example L. I. Zakharkin and V. V. Gavrilenko, *Journal of General Chemistry of the U.S.S.R.*, 1962, 32, 688; and E. Schaschel and M. C. Day, *J. Am. Chem. Soc.*, 1968, 90, 503. Mixtures of alkali metal salts, particularly sodium and potassium, of tetraalkylaluminates have been reported and used. See for example U.S. Pat. No. 3,234,115 and U.S. Pat. No. 3,969,195. Another way of naming an alkali metal salt of a tetraalkylaluminate is as an alkali metal aluminum alkyl, for example, sodium aluminum tetraethyl, which is synonymous with sodium tetraethylaluminate.

One reference to sodium potassium alloy in connection with a tetraalkylaluminate is found in U.S. Pat. No. 3,285,947, issued to Ziegler and Lehmkuhl, from column 1, line 71 to column 2, line 6, which describes a reaction of sodium tetraethylaluminate to form potassium tetraethylaluminate, and states > When stirring [sodium tetraethylaluminate] with metallic potassium, sodium will be liberated. The latter forms an alloy with potassium and the result hereof is that finally hardly more than 80 mol percent of potassium compounds in addition to 20 mol percent of sodium compound are present in the final product. Moreover, the establishment of equilibrium which is obviously present takes an extended period of time.

This disclosure, however, is non-enabling for efficient production of tetraalkylaluminates as mixtures of their sodium and potassium salts. No further information is given regarding the solvent used (or lack thereof); what temperatures, if other than room temperature, were employed; what other pertinent conditions, if any, were used in attempting the reaction described; or how long it takes for the equilibrium to be established. On the other hand, this description does make clear that some sodium potassium alloy remains in the reaction mixture at the end (because the reaction does not proceed to completion), an undesirable result for Ziegler and Lehmkuhl because 100% yield of the potassium salt was desired, in addition to the presence of the remaining sodium potassium alloy. Additionally, U.S. Pat. No. 3,285,947 also discloses at column 1, lines 55–62, that in the reaction

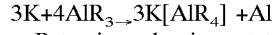

> Potassium aluminum tetraethyl produced in this manner has been found to contain always certain impurities which can be removed only with great difficulties by recrystallization. The raw product of this reaction is brown-colored and can hardly be obtained completely colorless by the purification.

Thus, U.S. Pat. No. 3,285,947 teaches away from reacting potassium metal with trialkylaluminum compounds to obtain potassium tetraalkylaluminates because of the concurrently-formed, persistent impurities.

SUMMARY OF THE INVENTION

This invention provides a simple, direct method for the preparation of mixtures of sodium and potassium salts of tetrahydrocarbylaluminates. The use of sodium potassium alloy enables the preparation of both salts in the same reaction zone at the same time. Further, the preparation can be conducted in the absence of solvent, avoiding potentially undesirable side products which are often produced when such a reaction is conducted in certain solvents, including aromatic solvents such as toluene.

In contrast to the above teachings of U.S. Pat. No. 3,285,947, the present invention employs a trihydrocarbylaluminum compound to form the mixture instead of starting from sodium tetraethylaluminate. Further, sodium tetraethylaluminate, the starting material in U.S. Pat. No. 3,285,947, must be preformed. In comparison, the present invention provides a one-step process in which the mixture of sodium and potassium salts are made directly from a trihydrocarbylaluminum compound and sodium potassium alloy, without any sodium potassium alloy remaining at the end of the process. This contrasts with the sodium tetraethylaluminate process in U.S. Pat. No. 3,285,947, in which some sodium potassium alloy remains when equilibrium is reached (i.e., the reaction ends). In addition, the yields in the present invention, based on sodium potassium alloy, are quantitative. An advantage of the process of the present invention is that aluminum metal is formed as a side product, and can be used to form more trihydrocarbylaluminum, if desired. A further advantage provided by the present invention is that no undesirable, persistent impurities are formed when using a trihydrocarbylaluminum compound and sodium potassium alloy to form a tetrahydrocarbylaluminate as a mixture of its sodium and potassium salts. Why this is so is not known.

One embodiment of this invention is a process for preparing a tetrahydrocarbylaluminate. This process comprises contacting sodium potassium alloy and at least one trihydrocarbylaluminum compound such that a tetrahydrocarbylaluminate is formed as a mixture of its sodium salt and potassium salt. Aluminum metal is formed as a coproduct in this process.

Sodium metal, potassium metal, and most trihydrocarbylaluminum compounds are oxygen and water sensitive. Although less reactive than sodium potassium alloy, the aluminum metal coproduct of the process is also oxygen and water sensitive. Thus, the minimization of oxygen and water in all manipulations of these substances is recommended and preferred.

These and other embodiments and features of this invention will be still further apparent from the ensuing description and appended claims.

FURTHER DETAILED DESCRIPTION OF THE INVENTION

Sodium potassium alloy is sometimes referred to as sodium/potassium alloy or sodium-potassium alloy. Sodium potassium alloy is also referred to by a combination of the two chemical elements' abbreviations, i.e., Na/K or NaK.

Sodium potassium alloy, as is well known in the art, is made by mixing sodium metal and potassium metal. The mole ratio of sodium to potassium in the alloy determines the mole ratio of sodium tetrahydrocarbylaluminate to potassium tetrahydrocarbylaluminate in the product. Generally, the ratio of sodium to potassium may be varied widely along a continuum from predominately sodium to predominately potassium. Generally, mole ratios of sodium to potassium are in the range of about 100:1 to about 1:100. Preferred mole ratios of sodium to potassium in the alloy are in the range of about 25:1 to about 1:25, and more preferably are in the range of about 10:1 to about 1:10. Most preferred in the alloy is a mole ratio of sodium to potassium in the range of about 5:1 to about 1:5. The mole ratio of sodium tetrahydrocarbylaluminate to potassium tetrahydrocarbylaluminate is generally determined by the mole ratio of sodium to potassium in the sodium potassium alloy, and thus it is straightforward to form a tetrahydrocarbylaluminate salt in the desired proportion of sodium salt to potassium salt.

The trihydrocarbylaluminum compound has three hydrocarbyl groups which may be the same or different. It is usually preferred that all three hydrocarbyl groups are the same, as a product with four hydrocarbyl groups that are all the same are normally desired. If a product with a mixture of hydrocarbyl groups is desired, a trihydrocarbylaluminum compound in which at least one hydrocarbyl group is different than the other two hydrocarbyl groups may be employed. Another method to achieve a tetrahydrocarbylaluminate with a mixture of hydrocarbyl groups is to use two or more different trihydrocarbylaluminum compounds. Preferred trihydrocarbylaluminum compounds have hydrocarbyl groups which have from one to about twenty carbon atoms; it is also preferred that these hydrocarbyl groups are alkyl groups.

It is to be understood that small amounts of impurities, usually one or more other trihydrocarbylaluminum compounds and/or one or more dihydrocarbylaluminum compounds, are often present with the desired trihydrocarbylaluminum compound(s), and these impurities may contribute to the formation of a small amount of an undesired aluminate salt. As an example of impurities, small amounts of butyldiethylaluminum and diethylaluminum are present in some formulations of triethylaluminum.

Trihydrocarbylaluminum compounds that can be used in the practice of this invention include, but are not limited to, trimethylaluminum, triethylaluminum, dimethylethylaluminum, diethylmethylaluminum, tri-n-propylaluminum, triisopropylaluminum, tri-n-butylaluminum, triisobutylaluminum, diisobutylethylaluminum, tri-tert-butylaluminum, tri-3-methylbutylaluminum, tripentylaluminum, tricyclopentylaluminum, trihexylaluminum, triisohexylaluminum, tri-3-methylpentylaluminum, tri-4-methylpentylaluminum, tri-2-methylhexylaluminum, tri-3-methylhexylaluminum, tri-2-ethylhexylaluminum, tricyclohexylaluminum, tri(methylcyclohexyl)aluminum, triheptylaluminum, trioctylaluminum, tri-n-decyl aluminum tridodecylaluminum, trihexadecylaluminum, triphenylaluminum, tritolylaluminum, tris(3,5-dimethylphenyl)aluminum, tris(2,4-diisopropylphenyl) aluminum, tribiphenylylaluminum, diphenyl(methyl)aluminum, dimethyl(phenyl) aluminum, ethylmethylphenylaluminum, tri-α-naphthylaluminum, tri-β-naphthylaluminum, and the like, and mixtures of two or more of the foregoing compounds. Preferred trihydrocarbylaluminum compounds are trimethylaluminum, triethylaluminum, and tri-n-propylaluminum, and mixtures of at least two of these. More preferred are trimethylaluminum and triethylaluminum; most preferred is triethylaluminum.

Most trihydrocarbylaluminum compounds are liquid, and thus can act as a solvent for the process. Advantageously, this minimizes the number of components that need to be brought into the reaction zone, and furthermore, avoids the formation of metallated aromatic species, which are often undesirable side products which form when an alkali metal comes into contact with an aromatic solvent. Additional advantages that have been observed when conducting the process in the absence of ancillary solvent include the minimization of the formation of aluminum hydride, and the formation of fewer colored impurities. Yet another advantage of the process of the present invention is that, at the end of the process, all of the sodium potassium alloy is consumed. Thus, if desired, an aromatic solvent may be introduced at the end of the process, e.g., for workup of the reaction products, without deleterious effect.

When an ancillary solvent is used in the process of preparing a tetrahydrocarbylaluminate, such solvent may be a saturated hydrocarbon, aromatic hydrocarbon, or an ether. Suitable saturated hydrocarbons include pentane, hexane, cyclohexane, methylcyclohexane, heptane, cyclooctane, nonane, and the like. Preferred saturated hydrocarbons are hexane, cyclohexane, and heptane. Aromatic hydrocarbons that can be used include benzene, toluene, xylene, mesitylene, ethylbenzene, diethylbenzene, 1,2,4-triethylbenzene, 1,3,5-triethylbenzene, amylbenzene, tetrahydronaphthalene, and the like. Toluene and ethylbenzene are preferred aromatic hydrocarbons. Ethers that can be used include diethyl ether, ethyl n-propyl ether, di-n-propyl ether, diisopropyl ether, di-n-butyl ether, tetrahydrofuran, methyltetrahydrofuran, cyclohexylmethyl ether, 1,4-dioxane, 1,3-dioxolane, glyme (the dimethyl ether of ethylene glycol), diglyme (the dimethyl ether of diethylene glycol), triglyme, tetraglyme, and the like. Preferred ethers are diethyl ether and tetrahydrofuran. However, it is preferred to perform the process of the invention without such ancillary solvent.

Alkali metal tetrahydrocarbylaluminates, including those produced by the process of the invention, are generally solids. Thus, especially when no ancillary solvent is employed in the process, it is preferred to use an excess of the trihydrocarbylaluminum compound relative to sodium potassium alloy. Yields of the tetrahydrocarbylaluminate salts are quantitative based on sodium potassium alloy, which normally is completely consumed when excess trihydrocarbylaluminum compound is present.

In the process of the invention, the sodium potassium alloy and the trihydrocarbylaluminum compound can be brought together in any order. The sodium potassium alloy can be formed in the presence of the trihydrocarbylaluminum compound (i.e., in situ). Sodium potassium alloy can be present in the reaction zone prior to the introduction of the trihydrocarbylaluminum compound, or introduced after the trihydrocarbylaluminum compound is introduced to the reaction zone, or both the sodium potassium alloy and the trihydrocarbylaluminum compound can be introduced to the reaction zone at the same time. Because the reaction is exothermic, it is preferred to bring the sodium potassium alloy and trihydrocarbylaluminum compound into contact with one another slowly. This can be achieved by adding one component slowly to the other (e.g., sodium potassium alloy to the trihydrocarbylaluminum compound, or trihydrocarbylaluminum compound to sodium potassium alloy), or by contacting small amounts of each component per unit time when introducing them to the reaction zone at the same time. On the laboratory scale, addition times can be an hour or less, but may be longer, depending on the scale of the reaction.

The reaction of the trihydrocarbylaluminum compound with sodium potassium alloy is fast; it is believed to occur upon contact of the reagents. It may be preferable to stir the reaction mixture for two or three hours or longer, on the laboratory scale, to ensure that all of the components have come into contact. Vigorous agitation is typically employed to ensure thorough mixing and good contact of the alloy and the trihydrocarbylaluminum compound. Stirring rates in the range of about 150 rpm to about 250 rpm were found to be effective on the laboratory scale.

In the absence of ancillary solvent, room temperature is not a desired reaction condition because the tetrahydrocarbylaluminate salts are solid at room temperature, at which condition the salts often coat the sodium potassium alloy, thereby preventing further reaction. Temperatures for the process in the absence of ancillary solvent on the laboratory scale are generally in the range of about 50° C. to about 150° C., and preferably are in the range of about 60° C. to about 150° C. The most preferred temperatures when operating in the absence of solvent are in the range of about 80° C. to about 120° C.

When the process is performed in the presence of ancillary solvent (in which the tetrahydrocarbylaluminate salts would be dissolved), lower temperatures become practical. For example, on the laboratory scale, a reaction of sodium potassium alloy with triethylaluminum in toluene works at temperatures as low as about 30° C. to about 40° C. As long as the solvent mixture does not freeze, temperatures as low as about −95° C. are possible in performing the process of the invention. Naturally, the reaction is expected to occur more slowly at such low temperatures, but in some instances this may be desirable.

The following examples are presented for purposes of illustration, and are not intended to impose limitations on the scope of this invention.

EXAMPLES

All procedures were carried out in a nitrogen-purged glove box. Reaction product mixtures were filtered by transferring them through a ¼-inch outer diameter PTFE dip tube having a medium (10–15 μm) glass frit at its inlet. In all of the Examples, the triethylaluminum used was Albemarle Corporation's UltraLow Hydride TEA (23.0 Wt % Al; 91.32 mole % $Et_3Al$; 8.68 mole % $BuAlEt_2$; trace amounts of $HAlEt_2$, too small to quantify). Conductivities were determined at 95° C. with a digital conductivity meter (VWR International, West Chester, Pa., #23226-523) that was equipped with a glass/platinum conductivity probe (VWR, # 232226-524). The conductivity meter was calibrated using conductivity calibration standards (aqueous potassium chloride solutions, VWR, #s 23336-603, -625, & -647). Solution colors were evaluated by Hunter colorimetry using an air-filled cell as the reference. In the Hunter colorimetry, the "L" value indicates light transmittance: 0=no light transmitted, 100=all light transmitted; the "a" value indicates red (positive numbers) or green (negative numbers); and the "b" value indicates yellow (positive numbers) or blue (negative numbers).

In the Tables, ND signifies that the analysis was done, but nothing was detected. Et—Al, Bu—Al, H—Al are, respectively, ethyl groups, butyl groups, or hydride bound to aluminum. Metallated aromatics families #1 and #2 have proton NMR resonances at about 2.2 and 2.6 ppm, respectively. Concentrations were estimated assuming the signals were due to methyl groups attached to metallated aromatic rings, with one methyl group per ring.

Example 1

No Solvent Present During Initial Na/K+Triethylaluminum Reaction

A 3-liter jacketed round-bottomed flask, which was equipped with a 113-mm diameter, carbon steel, mechanically driven stirring paddle, was charged with neat triethylaluminum (272.35 g, 2.326 mol) which was then heated to ~85° C. Na/K was made by melting together sodium metal and potassium metal in 1:4 (Na:K) molar proportions in a glass beaker, and Na/K was forced through a medium glass frit (10–15 μm) just before entering the reactor. While stirring at 200 rpm, and with 85° C. oil circulating through the reactor's jacket, a total of 44.4 g (1.24 mol) of Na/K alloy was added to the reactor in 5- to 10-gram portions during about 45 minutes. After each portion of Na/K alloy was added, the reaction temperature increased by ~10° C. to ~15° C., and it was allowed to cool to ~85° C. to ~90° C. before adding the next portion of Na/K. As the last portions of Na/K were added, the reaction mixture became inhomogeneous, consisting of, at 85° C., a milky-white, semi-solid gel phase and a clear liquid phase, both of which contained finely divided gray aluminum metal. After stirring for another ~30 minutes at 85° C., the stirrer and the oil circulator & heater were turned off, and the reaction mixture slowly cooled to room temperature overnight, after which the white gel phase solidified and the reaction product mixture consisted of a water-clear liquid phase (~50 to ~100 mL) above the white solid. A portion of the liquid phase (4.56 g) was removed and analyzed (Sample 1-1); the results are summarized in Table 1.

Toluene (252.1 g) was added to the reactor and the mixture was heated to 80° C. and stirred until the white solid dissolved (~1 hour). The solution was then filtered and the reactor and the aluminum metal by-product were washed with two portions of toluene (~40-g each), yielding 554 g of filtrate (Sample 1-2; see Table 1).

Additional triethylaluminum (61.77 g, 0.5277 mol) and toluene (90.6 g) were added to the filtrate and the solution was stirred with a PTFE-coated magnetic stirring bar while warming to ~60° C., and kept stirring at ~60° C. for about 3 hours. Data obtained on the final solution (Sample 1-3) are summarized in Table 1. The conductivity of Sample 1-3 was 14.2 mS/cm at 95° C.; Hunter colorimetry values were L=102; a=−0.2; and b=0.7, where the meanings of L, a, and b are as described above.

TABLE 1

| Sample | $(CH_3CH_2)_3Al$ | 1-1 | 1-2 | 1-3 |
|---|---|---|---|---|
| Toluene | ND | ND | 50.8 wt % | 49.8 wt % |
| Al | 23.3 wt % | 21.8 wt % | 8.19 wt % | 8.91 wt % |
| K | | <0.1 wt % | 6.11 wt % | 5.13 wt % |
| Na | | 0.0090 wt % | 0.946 wt % | 0.760 wt % |
| Et—Al | 25.8 wt % | 24.4 wt % | 11.1 wt % | 11.5 wt % |
| Bu—Al | 0.78 wt % | 1.63 wt % | 0.36 wt % | 0.37 wt % |
| H—Al | trace | trace | trace | 0.03 wt % |
| Metallated Aromatic #1 | ND | | | |
| Metallated Aromatic #2 | ND | | | |

Example 2

No Solvent Present During Initial Na/K+Triethylaluminum Reaction

The equipment and chemicals were the same as those used in Example 1. The reactor was first charged with freshly filtered Na/K alloy (51.04 g, 1.423 mol, Na:K mole ratio=1:4), then it was heated to 87° C., after which triethylaluminum (334.0 g, 2.853 mol) was fed over about half an hour while stirring at 219 rpm. As the first several grams of triethylaluminum were added, the surface of the Na/K alloy turned black, "smoke" formed in the head space, and the reaction temperature increased to ~95° C., where it remained until almost all of the triethylaluminum had been added. The reaction mixture was a black slurry until about a third of the triethylaluminum had been added, when the color turned to gray. After adding all of the triethylaluminum, the reaction mixture was stirred at ~87° C. for another hour, and then a ~1 gram, inhomogeneous sample was removed and analyzed by proton NMR spectroscopy. After stirring and heating for another two hours, a similarly inhomogeneous ~3 gram sample was removed and analyzed by proton NMR spectroscopy. There was no evidence of any reaction occurring in the final two hours.

The stirrer and the oil circulator & heater were turned off and the reaction mixture slowly cooled to room temperature overnight, after which the white gel phase solidified and the reaction product mixture consisted of a clear liquid phase above the white solid. Toluene (305.9 g) was added, and the oil circulator & heater were turned on with the circulator's thermostat set to 90° C. When the temperature of the reaction product mixture reached 60° C., its viscosity became low enough to stir the mixture, and the mixture was stirred at ~200 rpm while warming to 88° C., during which time the white semi-solid dissolved and the solution became water-clear except for the aluminum metal by-product. The solution was cooled to 50° C. and a 10 gram sample was removed and filtered through a 0.2 μm PTFE syringe filter to remove aluminum metal. Analytical data obtained on the filtrate (Sample 2-1) are summarized in Table 2.

Additional triethylaluminum (45.06 g, 0.3849 mol) and toluene (134.1 g) were added, the mixture was stirred at room temperature for several minutes, and then it was filtered. Analytical data obtained on this filtrate (762.6 g, Sample 2-2) are summarized in Table 2. The conductivity of Sample 2-2 was 14.6 mS/cm at 95° C.; Hunter colorimetry values were L=103; a=−0.6; and b=2, where the meanings of L, a, and b are as described above.

TABLE 2

| Sample | $(CH_3CH_2)_3Al$ | 2-1 | 2-2 |
|---|---|---|---|
| Toluene | ND | 44.3 wt % | 50.4 wt % |
| Al | 23.3 wt % | 9.52 wt % | 8.90 wt % |
| K | | 6.62 wt % | 5.26 wt % |
| Na | | 0.953 wt % | 0.760 wt % |
| Et—Al | 25.8 wt % | 12.6 wt % | 11.4 wt % |
| Bu—Al | 0.78 wt % | 0.36 wt % | 0.34 wt % |
| H—Al | trace | 0.02 wt % | 0.04 wt % |
| Metallated Aromatic #1 | ND | ND | ND |
| Metallated Aromatic #2 | ND | ND | ND |

Example 3

Toluene Present During the Na/K+Triethylaluminum Reaction; Na/K Alloy was Made In Situ The equipment and chemicals were the same as those used in Examples 1 and 2, except that the reactor was equipped with a reflux condenser, which was cooled with ~10° C. oil.

The 3-L reactor was charged with toluene (160.0 g), which was then heated to ~65° C. to ~70° C., after which potassium metal (23.47 g, 0.6003 mol) and then sodium metal (3.46 g, 0.150 mol) were added while stirring at ~200 rpm. The resulting mixture of toluene and Na/K alloy was heated to ~111° C. (toluene reflux) and then triethylaluminum (185 g, 1.62 mol) was added over ~90 minutes, after which the triethylaluminum supply bottle and feed lines were washed twice with toluene (11.0 g, 5.6 g). The stirrer speed was then increased to 250 rpm, and the reaction mixture was stirred for another ~15 minutes, after which the thermostat of the oil circulator that was plumbed to reactor's jacket was set to 8° C., and a ~15 mL sample of the product solution was removed when the mixture had cooled to ~85° C. This sample was filtered through a 1.0 μm PTFE syringe filter while still hot, and the filtrate (Sample 3-1) was analyzed. Data are summarized in Table 3. Proton NMR spectroscopy showed that the filtrate contained at least two different families of metallated aromatic species. One family had several minor NMR peaks at about 2.2 ppm, while the second family had several minor peaks at about 2.6 ppm.

The reactor was left unstirred at ~8° C. for ~36 hrs, and then another ~15 mL sample (Sample 3-2) was removed, filtered through a 1.0-μm PTFE syringe filter, and analyzed. Its composition was much like that of the first 15 mL sample, except that it contained more toluene, and correspondingly lower concentrations of the other constituents except for sodium, probably because significant amounts of toluene had evaporated from the first sample because it was handled while hot. A significant quantity of sodium went into solution after Sample 3-1 was taken. Data are summarized in Table 3.

The composition of the reaction product mixture was adjusted by adding triethylaluminum (20.00 g, 0.1708 mol), potassium metal (1.48 g, 0.0378 mol), and toluene (55.10 g), and then heating to 73° C. while stirring at 150 rpm for 3 hours, after which the stirrer and the oil circulator & heater were turned off, allowing the mixture to slowly cool to room temperature. A ~30 mL sample (Sample 3-3) was removed and filtered through a 1.0 μm PTFE syringe filter. The analytical data are summarized in Table 3. The conductivity of Sample 3-3 at 95° C. was 21.4 mS/cm.

The rest of the reaction product mixture was filtered two days later. Analytical data for the filtrate (380.4 g, Sample 3-4) are summarized in Table 3. The conductivity of Sample 3-4 was 18.7 mS/cm at 95° C.; Hunter colorimetry values were L=98; a=−1; and b=12, where the meanings of L, a, and b are as described above.

TABLE 3

| Sample | (CH₃CH₂)₃Al | 3-1 | 3-2 | 3-3 | 3-4 |
|---|---|---|---|---|---|
| Toluene | ND | 40.6 wt % | 44.5 wt % | 47.3 wt % | 47.4 wt % |
| Al | 23.3 wt % | 10.2 wt % | 9.62 wt % | 9.27 wt % | 9.33 wt % |
| K | | 6.21 wt % | 5.79 wt % | 5.42 wt % | 5.45 wt % |
| Na | | 0.942 wt % | 0.959 wt % | 0.766 wt % | 0.772 wt % |
| Et—Al | 25.8 wt % | 12.3 wt % | 12.1 wt % | 11.2 wt % | 10.9 wt % |
| Bu—Al | 0.78 wt % | 0.43 wt % | 0.40 wt % | 0.39 wt % | 0.32 wt % |
| H—Al | trace | 0.34 wt % | 0.25 wt % | 0.32 wt % | 0.32 wt % |
| Metallated Aromatic #1 | ND | 0.17 wt % | 0.21 wt % | 0.12 wt % | 0.13 wt % |
| Metallated Aromatic #2 | ND | 0.10 wt % | 0.12 wt % | 0.10 wt % | 0.10 wt % |

Example 4

Toluene Solvent Present During the Na/K+Triethylaluminum Reaction; Na/K Alloy was the First Ingredient Charged The equipment and chemicals were the same as those described in Example 3. Potassium metal (22.85 g) and sodium metal (3.36 g) were melted together in a glass beaker, yielding liquid Na/K alloy covered by a thin layer of dark gray, somewhat fibrous, material that appeared to be solid or semi-solid. The 3 L reactor was charged with 21.85 g of clean, liquid alloy that was syringed from the bottom of the beaker, followed by a charge of toluene (130.14 g). After warming to 35° C., triethylaluminum (150.33 g, 1.282 mol) was added over 75 minutes while stirring at 180 rpm. The triethylaluminum feed bottle and lines were then washed twice with toluene (17.5 g, 18.8 g), the reaction mixture was stirred at 180 rpm for another 4 hours, and then a 10 mL sample (Sample 4-1) was removed, filtered, and analyzed; data are summarized in Table 4. The reaction mixture was stirred at 180 rpm for another 3 hours at 35° C., and then was left unstirred at ~22° C. for 60 hours, after which another 10 mL sample (Sample 4-2) was removed, filtered, and analyzed. There was no evidence of any reaction occurring after Sample 4-1 was taken.

Triethylaluminum (5.0 g) and toluene (18.0 g) were added to the reaction product mixture. After stirring for about an hour at room temperature, a 10 mL sample (Sample 4-3) was removed, filtered and analyzed.

The rest of the product solution was filtered eight days later. Analytical data for the filtrate (275.4 g, Sample 4-4) are summarized in Table 4. The conductivity of Sample 4-4 was 14.8 mS/cm at 95° C.; Hunter colorimetry values were L=91; a=−2; and b=26, where the meanings of L, a, and b are as described above.

TABLE 4

| Sample | (CH₃CH₂)₃Al | 4-1 | 4-2 | 4-3 | 4-4 |
|---|---|---|---|---|---|
| Toluene | ND | 47.2 wt % | | 49.9 wt % | 49.1 wt % |
| Al | 23.3 wt % | 9.25 wt % | 9.18 wt % | 8.89 wt % | 9.05 wt % |
| K | | 5.78 wt % | 5.71 wt % | 5.34 wt % | 5.44 wt % |
| Na | | 0.814 wt % | 0.807 wt % | 0.751 wt % | 0.763 wt % |
| Et—Al | 25.8 wt % | 11.24 wt % | | 10.9 wt % | 10.98 wt % |
| Bu—Al | 0.78 wt % | 0.36 wt % | | 0.39 wt % | 0.35 wt % |
| H—Al | trace | 0.22 wt % | | 0.26 | 0.22 wt % |
| Metallated Aromatic #1 | ND | 0.08 wt % | | 0.08 | 0.08 wt % |
| Metallated Aromatic #2 | ND | 0.08 wt % | | 0.09 | 0.08 wt % |

Table 5 summarizes the conductivity and colorimetry data described in the above Examples. Sample numbers correspond to the same samples as in the above Examples.

TABLE 5

| Sample | 1-3 | 2-2 | 3-3 | 3-4 | 4-4 |
|---|---|---|---|---|---|
| Conductivity | 14.2 mS/cm | 14.6 mS/cm | 21.4 mS/cm | 18.7 mS/cm | 14.8 mS/cm |
| Color | | | | | |
| L | 102 | 103 | | 98 | 91 |
| a | −0.2 | −0.6 | | −1 | −2 |
| b | 0.7 | 2 | | 12 | 26 |

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation within the spirit and scope of the appended claims.

What is claimed is:

1. A process for producing at least one tetrahydrocarbylaluminate, which process comprises contacting sodium potassium alloy and at least one trihydrocarbylaluminum compound such that a tetrahydrocarbylaluminate is formed as a mixture of its sodium salt and potassium salt.

2. A process according to claim 1 wherein said process is conducted in the absence of an ancillary solvent.

3. A process according to claim 2 wherein the temperature is in the range of about 60° C. to about 150° C.

4. A process according to claim 2 wherein the temperature is in the range of about 80° C. to about 120° C.

5. A process according to claim 1 wherein said process is conducted in the presence of an ancillary solvent.

6. A process according to claim 1 wherein the mole ratio of sodium to potassium in said alloy is in the range of about 25:1 to about 1:25.

7. A process according to claim 1 wherein the mole ratio of sodium to potassium in said alloy is in the range of about 10:1 to about 1:10.

8. A process according to claim 1 wherein the mole ratio of sodium to potassium in said alloy is in the range of about 5:1 to about 1:5.

9. A process according to claim 1 wherein said trihydrocarbylaluminum compound has hydrocarbyl groups which have from one to about twenty carbon atoms.

10. A process according to claim 2 wherein said trihydrocarbylaluminum compound has hydrocarbyl groups which have from one to about twenty carbon atoms, and wherein the mole ratio of sodium to potassium in said alloy is in the range of about 25:1 to about 1:25.

11. A process according to claim 10 wherein the temperature is in the range of about 60° C. to about 150° C.

12. A process according to claim 9 wherein said hydrocarbyl groups are alkyl groups.

13. A process according to claim 2 wherein said trihydrocarbylaluminum compound has hydrocarbyl groups which are alkyl groups, and wherein the mole ratio of sodium to potassium in said alloy is in the range of about 25:1 to about 1:25.

14. A process according to claim 13 wherein the temperature is in the range of about 60° C. to about 150° C.

15. A process according to claim 12 wherein said trihydrocarbylaluminum compound is trimethylaluminum, triethylaluminum, tri-n-propylaluminum, or mixtures of at least two of these.

16. A process according to claim 2 wherein said trihydrocarbylaluminum compound is trimethylaluminum, triethylaluminum, tri-n-propylaluminum, or mixtures of at least two of these, and wherein the mole ratio of sodium to potassium in said alloy is in the range of about 25:1 to about 1:25.

17. A process according to claim 16 wherein the temperature is in the range of about 60° C. to about 150° C.

18. A process according to claim 15 wherein said trihydrocarbylaluminum compound is triethylaluminum.

19. A process according to claim 2 wherein the mole ratio of sodium to potassium in said alloy is in the range of about 10:1 to about 1:10; wherein said trihydrocarbylaluminum compound is trimethylaluminum, triethylaluminum, tri-n-propylaluminum or mixtures of at least two of these; and wherein the temperature is in the range of about 60° C. to about 150° C.

20. A process according to claim 19 wherein said trihydrocarbylaluminum compound is triethylaluminum.

21. A process according to claim 20 wherein the temperature is in the range of about 80° C. to about 120° C.

22. A process according to claim 2 wherein the mole ratio of sodium to potassium in said alloy is in the range of about 5:1 to about 1:5; wherein said trihydrocarbylaluminum compound is triethylaluminum; and wherein the temperature is in the range of about 80° C. to about 120° C.

23. A process according to claim 1 wherein said process is conducted in the presence of an ancillary solvent, wherein the mole ratio of sodium to potassium in said alloy is in the range of about 25:1 to about 1:25; and wherein said trihydrocarbylaluminum compound has hydrocarbyl groups which have from one to about twenty carbon atoms.

24. A process according to claim 23 wherein said hydrocarbyl groups are alkyl groups.

25. A process according to claim 1 wherein said process is conducted in the presence of an ancillary solvent, wherein the mole ratio of sodium to potassium in said alloy is in the range of about 10:1 to about 1:10; and wherein said trihydrocarbylaluminum compound is trimethylaluminum, triethylaluminum, tri-n-propylaluminum, or mixtures of at least two of these.

26. A process according to claim 1 wherein said process is conducted in the presence of an ancillary solvent, wherein the mole ratio of sodium to potassium in said alloy is in the range of about 5:1 to about 1:5; and wherein said trihydrocarbylaluminum compound is trimethylaluminum, triethylaluminum, tri-n-propylaluminum, or mixtures of at least two of these.

27. A process according to claim 1 wherein an excess of the trihydrocarbylaluminum compound relative to sodium potassium alloy is used.

28. A process according to claim 2 wherein an excess of the trihydrocarbylaluminum compound relative to sodium potassium alloy is used.

* * * * *